Nov. 8, 1966 R. S. MOORE Plant Pat. 2,685
THUJA PLANT
Filed March 11, 1965
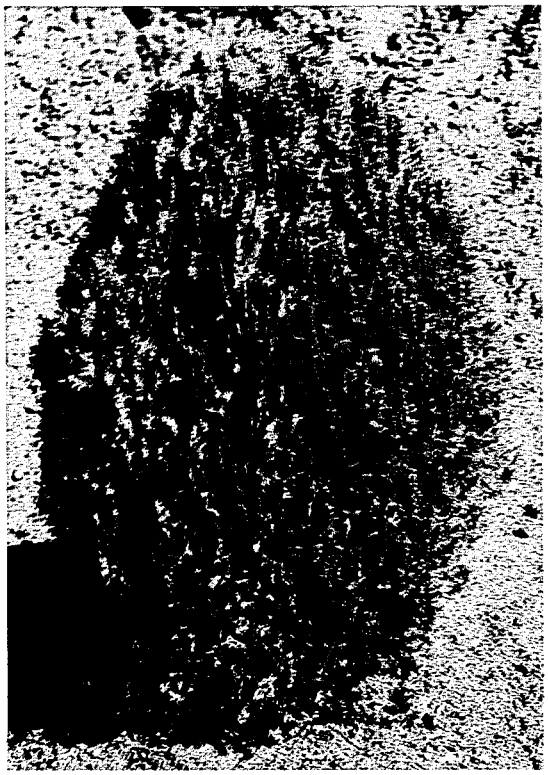
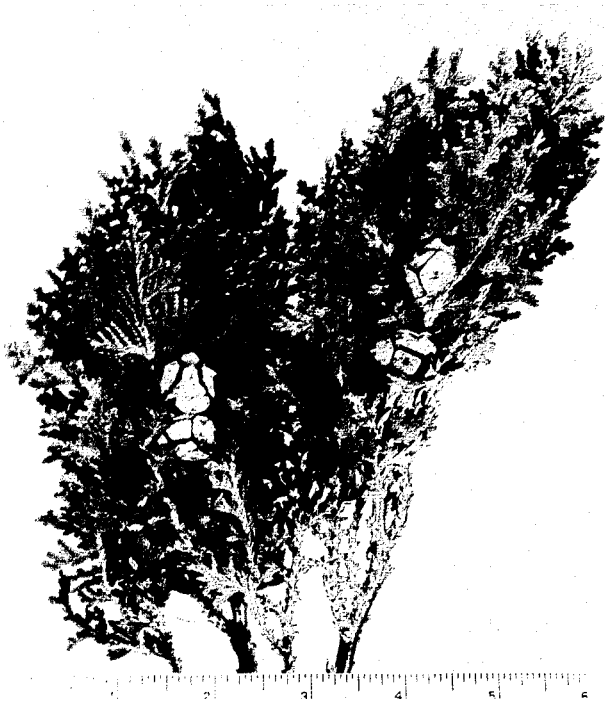
INVENTOR
RALPH S. MOORE
BY J. F. Cuneo
ATTORNEY United States Patent Office Plant Pat. 2,685
Patented Nov. 8, 1966

2,685
THUJA PLANT

Ralph S. Moore, Visalia, Calif., assignor to Monrovia Nursery Co., Azusa, Calif., a corporation of California Filed Mar. 11, 1965, Ser. No. 439,113
1 Claim. (Cl. Plt.—50)

The present discovery relates to a new and distinct variety of ornamental plant of the Thuja genus, that is a dwarf, is hardy, compact, and is particularly useful for landscaping.

The new variety was discovered by me in 1950 growing as a chance seedling in a bed of *Thuja orientalis aurea nana*, an unpatented variety, that was being cultivated by me on my property located at 2519 East Mineral King, Visalia, county of Tulare, State of California. The pollen parent is unknown.

While the new variety of Thuja resembles its seed parent, *Thuja orientalis aurea nana*, somewhat in coloration, which is a golden green, it differs from its seed parent in that the new variety is a dwarf and is considerably slower growing than its seed parent; plants that were started in 1954, were only ten inches high in 1957, and had a width of four inches. At the end of ten years these same plants had attained a height that varied between 30″ to 32″ and the average width of the plant was approximately 24″. The new variety also differs from its seed parent in that it has shorter and more tightly branched twigs and shoots, the shape of the plant is more rounded and less pointed, the entire plant is tightly compact, the foliage is stiff or "hard" to the touch; the leaf scales are tightly compact and are very closely spaced on the twigs and branches. The new variety differs substantially from the variety of *Thuja orientalis aurea nana* "Raffels," which is described as a smaller form of *nana*, in that the leaves of the new variety are longer, somewhat larger and more sharply pointed.

The foliage of the new variety is tightly knit and when handled the foliage feels very hard to the touch. The foliage of "Raffels" is more loosely knit and feels much softer to the touch when handled.

Another distinguishing characteristic of the new variety is that in the cold months of the year, its leaves turn a bluish green color while the leaves of "Raffels" retain their golden green coloration and show no appreciable change in color between summer and winter.

Some growers of the variety "Raffels" have reported that "Raffels" has a tendency of burning during very hot weather whereas the plants of the new variety have not exhibited this type of behaviour.

Plants of the new variety and those of "Raffels" have been raised in substantial numbers under identical growing conditions and even though the plants of the new variety are approximately six months older than those of "Raffels," they are all appreciably smaller in height and width than those of the variety "Raffels." As previously stated in the specification the new variety is a dwarf and is very slow growing.

The present variety has been asexually reproduced by me by means of cuttings. A notable characteristic of the new variety is that even though the cuttings are taken out of the normal season, regarded in California to extend from November to February, a relatively higher percentage of these cuttings will root than those taken out of season from the majority of the existing varieties of Thuja. The rooted cuttings grow into plants that can be marketed in a relatively short time but due to the fact that the new variety is a dwarf and that the plant is very slow growing, it would take a considerable period of time before a plant from such cuttings would reach any appreciable size. Asexual reproduction of the new and distinct variety has produced descendants that exhibit the foregoing characteristics which shows that the descendants are ture and that the new variety has become well established. The plant cannot be reproduced true from seed.

The accompanying drawings in full color show a view of a fully developed plant specimen and a view of a small branch of the new variety, the branch in the close-up view bearing cones.

The new and distinct variety retains its pleasant coloration throughout the year and due to its dwarf size and slow growth, the plant is ideal for tub use or for use in small containers. This new variety is ideally suited wherever a compact, oval-shaped evergreen plant is required.

The following is a detailed description of the new and distinct variety, and to assist in the identification of the important colors of the new variety, the nomenclature adopted by the British Horticultural Colour Charts has been followed.

*The plant*

General characteristics: The plant is a dwarf in size and is an upright, tightly compact bush that is best described as broadly conical and has a tip that is somewhat pointed.

Branches: The plant is fully branched at the base, all branches extending upwardly; the plant has no central leader or trunk. Color—light branches are light brown in color while the heavier branches are dark brown.

Branchlets: Extremely numerous, ascending; slender.

Leaves: Dense, compact leaf scales are short and are closely appressed, coming close to being imbricated.

*Shape.*—Rhombic ovate, acute, closely appressed.

*Color.*—Warm weather coloration: Leaves are bright green, coming close to Scheeles Green 860 or Scheeles Green 860/1, and shading to a lighter shade of green with the tips of all shoots being a golden green. Cold weather coloration: The leaves become a more bluish green with the advent of cold weather, the color coming close to Spinach Green o960/1. This color persists until the weather becomes warmer in the spring.

Flowers: The plant bears few flowers and those it does bear are characteristic of the species. Shape—small, globose, terminal on small branchlets.

Cones:

*Shape.*—Globose-ovate, comprising usually six ovate scales with a hornlike process.

*Size.*—The maximum size is ¾″ in length and having a maximum width of ¾″.

*Number.*—From none to a few. After fourteen years the original plant bore twelve cones. Plants that are eight years old have not borne any cones to date.

Seeds: The plants of this new variety have been observed to bear only a few seeds. Usually no seeds are produced.

I claim:

A new and distinct variety of Thuja plant substantially as shown and described, characterized by its dwarf size, its slow hardy growth habit, its many upwardly extending branches that start from the base with the absence of any central leader or trunk and forming a tightly compact bush that is broadly conical having a somewhat pointed tip, its shorter and more tightly branched twigs and shoots, and its foliage comprising leaf scales that are sharply pointed, tightly compact and closely spaced on the twigs and branches and feel stiff and hard to the touch, the color of the leaves being a golden green during the warm portion of the year and turning to a bluish green during the winter months.

No references cited.

ABRAHAM G. STONE, *Primary Examiner.*

ANTONIO F. GUIDA, *Examiner.*

R. E. BAGWILL, *Assistant Examiner.*